United States Patent [19]

Rifkin

[11] 4,292,139

[45] Sep. 29, 1981

[54] METHOD FOR INHIBITING DEPOSIT FORMATION IN DISTILLATION UNITS ASSOCIATED WITH SEPARATION AND PURIFICATION OF ALKYL PHOSPHOROCHLORIDOTHIOATES

[75] Inventor: Ellis B. Rifkin, Southfield, Mich.

[73] Assignee: Ethyl Corporation, Richmond, Va.

[21] Appl. No.: 202,126

[22] Filed: Oct. 30, 1980

Related U.S. Application Data

[63] Continuation-in-part of Ser. No. 74,505, Sep. 11, 1979, abandoned.

[51] Int. Cl.$^3$ .............................. B01D 3/34; C07F 9/02
[52] U.S. Cl. ........................................ 203/6; 203/60; 260/990
[58] Field of Search .................... 203/60, 6, 51, 59, 61, 203/57, 58; 260/990

[56] References Cited

U.S. PATENT DOCUMENTS

| | | | |
|---|---|---|---|
| Re. 26,330 | 1/1968 | Colfer | 208/48 |
| 3,089,890 | 5/1963 | Chupp et al. | 260/990 |
| 3,172,892 | 3/1965 | Le Suer et al. | 260/326.5 F |
| 3,271,296 | 9/1966 | Gonzalez | 203/6 |
| 3,356,774 | 12/1967 | Niermann et al. | 260/981 |
| 3,502,750 | 3/1970 | Angaret et al. | 260/986 |
| 3,836,610 | 9/1974 | Diveley | 260/986 |
| 3,856,898 | 12/1974 | Diveley | 260/990 |
| 3,897,523 | 7/1975 | Sorstokke | 260/986 |
| 4,025,586 | 5/1977 | Lippman | 260/990 |
| 4,159,289 | 6/1979 | Anderson | 260/990 |

Primary Examiner—Wilbur L. Bascomb, Jr.
Attorney, Agent, or Firm—Donald L. Johnson; Joseph D. Odenweller; John F. Hunt

[57] ABSTRACT

Deposit formation in distillation units, particularly column reboiler units, associated with the separation and purification of dialkyl phosphorochloridothioates from a crude material containing oxygenated compound impurities, is inhibited by incorporating in the feed stock a minor proportion (generally about 0.05 to about 15.0 weight percent) of an acylated amine prepared by reacting a hydrocarbon-substituted succinic compound with an alkylene amine or a hydroxyalkyl-substituted alkylene amine.

18 Claims, No Drawings

METHOD FOR INHIBITING DEPOSIT FORMATION IN DISTILLATION UNITS ASSOCIATED WITH SEPARATION AND PURIFICATION OF ALKYL PHOSPHOROCHLORIDOTHIOATES

CROSS-REFERENCE TO RELATED APPLICATION

This application is a Continuation-In-Part of pending application Ser. No. 074,505, filed Sept. 11, 1979, and now abandoned.

BACKGROUND OF THE INVENTION

The present invention relates to a method for reducing and/or preventing the fouling of process equipment in the preparation of O,O-di($C_1$-$C_8$ alkyl) phosphorochloridothioates. It is particularly applicable to process equipment involving the separation and purification of O,O-di($C_1$-$C_8$ alkyl) phosphorochloridothioates from a mixture thereof with certain impurities. Preferably, the improved method comprises adding to the crude dialkyl phosphorochloridothioate an acylated amine prepared by reacting a hydrocarbon-substituted succinic acid with an alkylene amine or a hydroxyalkyl-substituted alkylene amine. The O,O-dialkyl phosphorochloridothioates are valuable intermediates, for instance, in the preparation of lubricant additives and insecticides. Particularly, O,O-diethyl thiophosphoryl chloride is an intermediate in the synthesis of an insecticide known as parathion, and O,O-dimethyl thiophosphoryl chloride is an intermediate in the synthesis of the insecticide called methyl parathion. Such are also useful in the manufacture of diazinon, chlorpyrifus, fensulfothion and the like.

Several methods have been used for the synthesis of the esters of phosphorochloridothioic acid including one-step and two-step methods. In the one-step process, phosphorus pentasulfide, alcohol and chlorine are reacted to prepare the ester corresponding to the alcohol and then the solvent is removed and the product separated. Typical prior art patents disclosing a one-step process include U.S. Pat. Nos. 3,356,774 and 3,502,750. U.S. Pat. No. 3,356,774 discloses reacting a phosphorus pentasulfide suspension in an inert solvent at a temperature within the range of about 0° C. to about 150° C. with chlorine and an alcohol having 1 to 6 carbon atoms by introducing a stream of chlorine into said suspension and adding dropwise concurrently therewith the alcohol, allowing the chlorinating reaction to proceed to completion, expelling the solvent from the resulting reaction mixture and isolating O,O-dialkylthionophosphoric acid chloride by distillation. U.S. Pat. No. 3,502,750 discloses preparing lower alkyl esters of phosphorochloridothioic acid by reacting chlorine with a lower alkyl ester of dithiophosphoric acid and freeing the product of sulfur monochloride by reaction with hydrogen sulfide, preferably formed during the production of the dithiophosphoric acid ester by reaction of a lower alkanol with phosphorus pentasulfide.

In the two-step process, the first process step reacts phosphorus pentasulfide with an alcohol, such as ethanol, so as to form O,O-diethyl dithiophosphoric acid and hydrogen sulfide, and in a second process step the isolated O,O-diethyl dithiophosphoric acid is chlorinated in an appropriate solvent with chlorine gas, resulting in the formation of O,O-diethyl thiophosphoric acid chloride. Examples of prior art patents disclosing a two-step process include U.S. Pat. Nos. 3,836,610 and 3,856,898. In U.S. Pat. No. 3,836,610, the reaction mixture is chlorinated and then established and maintained at a temperature in the range of 85° C.–110° C. until it is substantially free of sulfur monochloride and the relatively thermal unstable sulfur that forms becomes more thermally stable so that the product dialkyl thiophosphoryl chloride can be readily and safely removed from the mixture thereof with sulfur by distillation. U.S. Pat. No. 3,856,898 discloses a process for treating a mixture comprising O,O-di($C_1$-$C_8$ alkyl) phosphorochloridothioate and amphorous sulfur at a concentration up to about one-third of the weight of the phosphorochloridothioate. In this process, the mixture is established in a first temperature range in which substantially all of the sulfur can go into solution without substantial decomposition of the phosphorochloridothioate, and maintained in that range until substantially all of the sulfur does go into solution. The resulting solution is established in a temperature range in which dissolved sulfur crystallizes, and is maintained in that range until sulfur crystallization is substantially complete. The crystallized sulfur then is separated by settlement (filtration, decantation, centrifugation, or the like) from the mother liquor. In one embodiment, the mother liquor, composed of the phosphorochloridothioate dissolved in a solvent, is treated by a procedure which includes distillation to obtain O,O-di($C_1$-$C_8$ alkyl) phosphorochloridothioate. Other prior art patents which disclose processes for preparing O,O-dialkyl phosphorochloridothioates include U.S. Pat. No. 3,897,523 which teaches a purification process in which the crude dialkyl phosphorochloridothioate is vaporized in a film evaporator, the vapor is condensed, washed with water at 10° C. to 60° C., the organic and aqueous phases separated and the organic phase vacuum dried; and U.S. Pat. No. 4,025,586, which discloses distilling the product dialkyl phosphorochloridothioate and water washing the distillation residue to hydrolyze impurities. The washed residue is then dried and recycled to the chlorination step. U.S. Pat. No. 3,089,890, teaches treating a distilled crude phosphorochloridothioate with water, separating the organic phase and drying to upgrade the crude and recover substantially contaminant-free phosphorochloridothioate. Most recently, U.S. Pat. No. 4,159,289 teaches a process for removal of sulfur impurities from phosphorochloridothioates by distillation in the presence of a naphthalenic liquid hydrocarbon sulfur solubilizing or suspending agent.

Conventionally, the alkyl groups in the dialkyl phosphorochloridothioates have from 1 to 8 carbon atoms and are generally selected from methyl, ethyl, isopropyl, butyl, sec.-butyl, t-butyl, and the like, up through n-octyl and isomers thereof. In each of these conventional one-step and two-step processes, however, impurities, such as phosphates are produced which cause severe fouling of the process equipment during separation and purification of product dialkyl phosphorochloridothioates. Although these various processes differ somewhat as to the precise manner in which product dialkyl phosphorochloridothioates are produced, those processes which involve the heating of a crude feed stock to a high temperature and the passage of such heated stock through a distillation column to separate and recover product dialkyl phosphorochloridothioate from the crude feed stock almost always result in the formation of some undesirable materials, believed principally to comprise oxygenated phosphorous compound impurities produced during production of the phosphorochloridothioates as by-products or from the thermal degradation of the desired dialkyl phohorochloridothioates during purification, along with impurities other than the aforementioned oxygenated phosphorus type impurities such as iron and/or sulfur or iron and sulfur containing compounds. These impurities solidify in and plug the distillation columns, and adhere to the walls of the tubes in the column reboiler sections of the columns as the impurities containing crude feed stock passes through or around the tubes. This lowers the efficiency, principally by impeding the flow of the feed stock therethrough, and the transfer of heat to or from such stock. After enough material has accumulated on the various parts on the reboiler units, usually the tube portions thereof, to lower efficiency substantially, the unit must be dismantled, cleaned and reassembled. Of course, such cleaning operations are not only tedious and costly, but result in a large proportion of "down-time" during which the unit is not functioning. Distillation alone cannot adequately remove these impurities.

The deposit formations resulting from the fouling phenomenon consist of a tacky, water soluble tar material believed to be composed principally of polyphosphates produced during the production of the phosphorochloridothioates as byproducts aforediscussed and/or from the desired product dialkyl phosphorochloridothioates which may be thermally degraded over time in the purification equipment to produce additional byproducts of the same sort. Specific impurities which are formed include diethylchlorophosphate, triethylthiophosphate, ethyldichlorophosphate and ethyldichlorothiophosphate. The thermal degradation of diethyl phosphorochloridothioate is illustrative of what may occur during processing operations. A sample of diethyl phosphorochloridothioate was found to contain 88.4 area percent diethyl phosphorochloridothioate and 0.48 area percent diethyl phosphoryl chloride by vapor phase chromatography. The sample was split in two parts and one was purged with air while the other was purged with nitrogen. The samples were heated at 140° C. for 3 hours. Samples taken after one-half hour and 3 hours were analyzed with the results shown below:

| Increase of Oxygenated Phosphorus Impurities with Time at 140° C. | | | |
|---|---|---|---|
| Time, hrs. | 0 | ½ | 3 |
| Air Purge | | | |
| Diethylphosphorochlorido-thioate (Area %) | 88.4 | 87.3 | 78.9 |
| Diethylphosphoryl chloride (Area %) | 0.48 | 0.59 | 2.4 |
| N₂ Purge | | | |
| Diethylphoschlorochlorido-thioate (Area %) | 88.4 | 87.1 | 71.4 |
| Diethylphosphoryl chloride (Area %) | 0.48 | 0.68 | 2.3 |

From the above data, it is clear that the impurity has increased fivefold while where was a 9–20% decrease in desired product. Such high impurity levels are not only undesirable for the aforediscussed fouling problems which they create in the distillation equipment, but are also undesirable because the end-product insecticides have been registered with governmental agencies as having been tested and found safe and effective with certain impurities at not greater than certain concentrations. Therefore, it is critical not only to prevent the fouling of process equipment by the impurities but also to maintain impurity identities and levels at or below those allowed in governmental registrations and as stated on label certifications for the end product.

Without limiting the invention in any manner and without advocating any particular mechanism or theory of action, it is believed that degradation of dialkyl phosphorochloridothioates could possibly take place according to the following chemical reaction scheme:

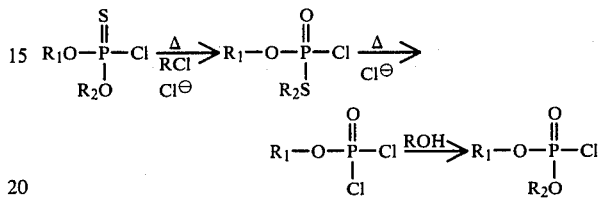

where $R_1$ and $R_2$ can be the same or different $C_{1-8}$ alkyl groups, the temperature ranges from 100°–150° C., and the necessary contact with ionic species is provided for a time sufficient to facilitate the degradation reaction. Further, it is believed that the presence of other impurities, such as sulfur, for example, in the form either of free sulfur or in some other form such as sulfur monochloride, formed as a by-product during the reaction; and/or iron which may be present in the crude feedstock or originate from deterioration of the metal in the process equipment may also either constitute a portion of the fouling deposits or alternatively exert a catalytic effect on and promote or increase the rate of phosphorus impurities formation. While fouling sometimes may be controlled by careful processing to obtain high purity crude feedstock by excluding impurities from the crude feed prior to separation and purification of product dialkyl phosphorochloridothioate therefrom, this is not altogether possible nor economically feasible in plant scale operation on a regular continuing basis.

Invention

It has now been found that deposit formation in the distillation units, particularly column reboiler units, used in the separation and purification of dialkyl phosphorochloridothioates from a crude mixture thereof containing certain oxygenated phosphorous compound impurities, can be prevented and/or inhibited simply without additional capital cost and with very small operational costs, by the addition to the crude dialkyl phosphorochloridothioate of a suitable treating agent.

Accordingly, it is an object of the present invention to inhibit and/or prevent the deposition and accumulation of harmful oxygenated phosphorus compound impurities in the distillation equipment, particularly the column reboiler units associated with the separation and purification of dialkyl phosphorochloridothioates formed during the separation and purification of product dialkyl phosphorochloridothioate from a crude feed stock thereof containing said oxygenated phosphorus compound impurities.

It is another object of the present invention to suspend or dissolve said oxygenated phosphorus compound impurities formed during the preparation and purification of product dialkyl phosphorochloridothioates in said feed stock thereby inhibiting their deposition and accumulation on various parts of the distillation equipment associated with the separation and purification of product dialkyl phosphorochloridothioates from a crude mixture thereof containing said oxygenated phosphorus compound impurities and allowing their removal from the column bottoms with the waste stream thereby leaving the column and column reboiler unit clean.

Yet another object of the present invention is to reduce the amount of "down-time" in the operation of the distillation equipment associated with the separation and purification of product dialkyl phosphorochloridothioates from a crude mixture thereof containing oxygenated phosphorus compound impurities thereby permitting the continuous distillation of said product dialkyl phosphorochloridothioates and thus avoiding batch distillation.

These and other objects of the invention are realized by the provision of a method for inhibiting or preventing the deposition and/or accumulation of oxygenated phosphorus compound impurities in the distillation column and column reboiler unit during the passage therethrough of a crude feed stock containing product dialkyl phosphorochloridothioates admixed with deposit-forming and fouling-causing oxygenated phosphorus compound impurities by dissolving in said feed stock a minor proportion, generally at least about 0.05 weight percent of about 15.0 weight percent and preferably about 0.1 weight percent to about 10.0 weight percent of an acylated amine prepared by mixing a hydrocarbon-substituted succinic acid or anhydride with an alkylene amine or a hydroxyalkyl-substituted alkylene amine.

Accordingly, a preferred embodiment of the present invention is a method for inhibiting or preventing the accumulation of oxygenated phosphorus compound impurities in the distillation columns and column reboiler units associated with the separation and purification of O,O-dialkyl phosphorochloridothioates from a crude feed stock containing said O,O-dialkyl phosphorochloridothioates admixed with deposit-forming and fouling-causing oxygenated phosphorus compound impurities which comprises distilling said O,O-dialkyl phosphorochloridothioate containing feed stock in the presence of a minor proportion of an acylated amine prepared by mixing a substituted succinic compound selected from the class consisting of substituted succinic acids having the structural formula:

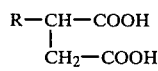

and substituted succinic anhydrides having the structural formula:

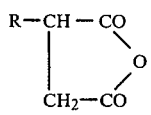

in which structural formulas R is a large, substantially aliphatic hydrocarbon radical having at least about 50 carbon atoms, with at least about one-half an equivalent amount of an ethylene amine and heating the resulting mixture to effect acylation and remove the water formed thereby.

In general, the process of the present invention proceeds initially as in any of the inherent above prior art patents until the step of separation of the product dialkyl phosphorochloridothioates from the reaction mixture. Accordingly, each of the above-mentioned patents contains valuable process information regarding the production of crude dialkyl phosphorochloridothioate useful in the practice of the present invention and the teachings of those references are hereby incorporated by reference as if fully set forth. The advantage obtained in the improved process of this invention is that the addition to the dialkyl phosphorochloridothioate containing crude of an acylated amine prevents or inhibits the accumulation of deposits in the distillation column and column reboiler formed primarily from oxygenated phosphorus compound impurities present in the crude feed stock during the separation and purification of product of dialkyl phosphorochloridothioate. The addition of the treating agent to the feed stock allows the use of a continuous column distillation system, reduces the amount of "down-time" in the operation of the continuous distillation, and provides a bottoms stream which contains the waste materials in a fluid or suspended state thereby allowing the product to be recovered from the overhead system and the waste stream to be easily removed for treatment or recycle. Typically, the crude dialkyl phosphorochloridothioates can have up to about 3% by weight of oxygenated phosphorus compounds, for example, diethyl chlorophosphate. Additionally, after formation, exposure of the product dialkyl phosphorochloridothioate to heat causes degradation and increases impurities such as dialkyl chlorophosphates. For example, distillation of diethyl chlorophosphate can increase the amount of diethyl phosphoryl chloride (i.e., diethyl chlorophosphate). Further, as aforementioned it is believed that the presence of other impurities, such as sulfur, for example, either in the form of free sulfur or in some other form, such as sulfur monochloride, formed as a by-product during the reaction; and/or iron, which may be present either in the crude feedstock or originate from deterioration of the metal in the process equipment may also contribute to the fouling deposits or, alternatively, exert a catalytic effect on and promote or increase the rate of phosphorus impurities formation. However, when separation or purification takes place in the presence of an acylated amine, as described in the present process, there is a marked decrease in the amount of oxygenated phosphorus compound impurities which accumulate in, and eventually plug the distillation equipment, i.e. the distillation column and column reboiler. Without being limited by any form or mode of action or theoretical mechanism of the invention, it is believed that the acylated amine reacts with the oxygenated phosphorus impurities selectively, altering their physical and/or chemical properties and allows the impurities to remain suspended or dissolved in the crude feed stock during separation and purification of the product dialkyl phosphorochloridothioates by means of conventional techniques. Any treating agent remaining after separation and purification of product dialkyl phosphorochloridothioates, remains suspended or dissolved in the bottoms stream which contains all of the waste materials in a fluid or suspended state and is eventually removed from the column bottoms where it is treated for waste deposit and/or recycle. Under these conditions, the impurities can be readily removed from the column bottoms with the waste stream, leaving the distillation column and column reboiler unit clean and the waste stream in an easily handled, pumpable form.

Thus, the acylated amine additive useful in this invention is one which when reacted with oxygenated phosphorus compound impurities produced in a process for preparing dialkyl phosphorochloridothioates will so alter the physical and chemical properties of the impurities by producing a reaction product that conventional techniques can be used to separate the reaction product from the dialkyl phosphorochloridothioate and that said impurities will not deposit in and foul the distillation equipment associated with the separation and purification of the desired dialkyl phosphorochloridothioate product.

The acylated amine required for the purpose of this invention is described in detail in U.S. Pat. No. 3,172,892. In the interest of not unduly lengthening the present specification it is intended that the disclosure of the said U.S. Pat. No. 3,172,892 be considered as forming a part of the present specification.

In summary, U.S. Pat. No. 3,172,892 deals with mixing a substituted succinic compound selected from the class consisting of substituted succinic acids having the structural formula

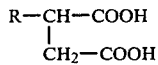

and substituted succinic anhydrides having the structural formula

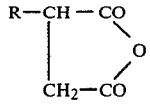

in which structural formulas R is a large, substantially aliphatic hydrocarbon radical having at least about 50 carbon atoms, with at least about one-half an equivalent amount of an ethylene amine, and heating the resulting mixture to effect acylation and remove the water formed thereby.

The reaction of this process, involving an amidation of a dicarboxylic acid (or anhydride thereof) with a polyamine, can result in a simple acyclic diamide, a cyclic diamide, a polymeric amide or a combination of any of these types of products. It will be noted also that the amide groups may react further to form imide groups and it is believed that a substantial amount of imide formation takes place in the process. Furthermore, there is reason to believe that in certain instances there is present in the product an appreciable proportion of amine carboxylate salt.

The size of the substituent of the succinic acid or anhydride is of major importance in the process because it allows the preparation of a product which satisfies the objects of the invention, i.e., one which is effective as an agent for preventing the accumulation of oxygenated phosphorus compound impurities in the purification equipment associated with the separation and purification of product dialkyl phosphorochloridothioates. It is important that this substituent be large, that it have at least about 50 carbon atoms in its structure. These substituent groups are substantially aliphatic hydrocarbon radicals, including both alkyl and alkenyl radicals. They are commonly derived from polyolefins such as polyethylene, polypropylene, polybutylene, etc., although they may be derived from any substantially aliphatic hydrocarbon.

The substituted succinic acids and anhydrides which are contemplated as a reactant in the process are readily available from the reaction of maleic anhydride with a high molecular weight olefin or a chlorinated high molecular weight olefin. The product from such a reaction is the corresponding alkenyl succinic anhydride. The reaction involves merely heating the two reactants at a temperature of about 150°-200° C. The reactions in each case are illustrated by the following equations.

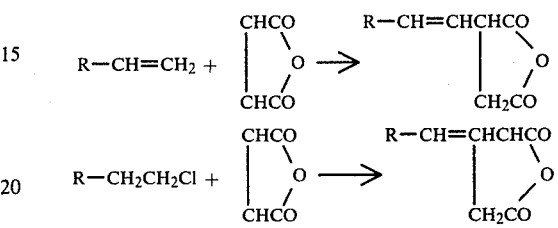

It will be appreciated that the reactions may not go precisely as indicated in the above equations, especially with respect to the particular carbon atom of the olefin or chloride reactant which ultimately becomes attached to the maleic acid or anhydride reactant, but other than this the equations are believed to be illustrative. Furthermore, although the product of this reaction has been indicated as being an alkenyl succinic anhydride it is apparent that similar products can be prepared by this process in which the substituent is something other than an alkenyl group. For the purposes of this invention this substituent should, however, be a substantially aliphatic group and in most cases of course it will be an alkyl or alkenyl group. In some cases, however, it may well be desirable to employ a substituted succinic anhydride in which the substituent is derived from a copolymer of styrene and isobutylene, or of a substituted styrene and some other aliphatic olefin. In these latter cases the copolymer will be substantially aliphatic, that is, the composition of the copolymer will be predominantly aliphatic, i.e., more than about 90%--the monomeric units will be those of the aliphatic monomer.

The most commonly used sources of these substantially aliphatic hydrocarbon substituents are the polyolefins. These are illustrated by polyethylene, polypropylene, polyisobutylene, etc. A particularly preferred polyolefin for this use is polyisobutylene. Thus, the condensation of a polyisobutylene having a molecular weight of 750 with maleic anhydride yields an alkenyl succinic anhydride which upon further reaction with an ethylene amine produces an especially effective antifouling agent. Polyisobutylenes of this particular molecular weight are quite economically available and the effectiveness of products prepared from this material makes this starting material particularly desirable for use in a process of this invention.

The substituted succinic anhydride ordinarily is reacted directly with the ethylene amine although in some circumstances it may be desirable first to convert the anhydride to the acid before reaction with diamine. In other circumstances it may be desirable to prepare the substituted succinic acid by some other means and to use an acid prepared by such other means in the process. In any event either the acid or the anhydride may be used in the process of this invention.

The term "ethylene amine" is used in a generic sense to denote a class of polyamines conforming for the most part of the structure

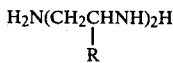

in which x is an integer and R is a low molecular weight alkyl radical or hydrogen. Thus, it includes for example ethylene diamine, diethylene triamine, triethylene tetramine, tetraethylene pentamine, pentaethylene hexamine, etc. These compounds are discussed in some detail under the heading "Ethylene Amines" in "Encyclopedia of Chemical Technology," Kirk and Othmer, vol. 5, pages 898-905, Interscience Publishers, New York (1950). Such compounds are prepared most conveniently by the reaction of ethylene dichloride with ammonia. This process results in the production of somewhat complex mixtures of ethylene amines, including cyclic condensation products such as piperazines and these mixtures find use in the process of this invention. On the other hand quite satisfactory products may be obtained also by the use of pure ethylene amines. An especially useful ethylene amine, for reasons of economy as well as effectiveness is a mixture of ethylene amines prepared by the reaction ethylene chloride and ammonia, having a composition which corresponds to that of tetraethylene pentamine. This is available from Carbide and Carbon under the trade name "Polyamine H."

It has been noted that at least one half of a chemical equivalent amount of the ethylene amine per equivalent of substituted succinic anhydride should be used in the process to produce a satisfactory product with respect to anti-fouling properties and generally it is preferred to use these reactants in equivalent amount. Amounts up to 2.0 chemical equivalents (per equivalent of substituted succinic anhydride) have been used with success, although there appears to be no advantage attendant upon the use of more than this amount. The chemical "equivalency" of the ethylene amine reactant is upon the nitrogen content, i.e., one having four nitrogens per molecule has four equivalents per mole.

The reaction of the process involves a splitting out of water and the reaction conditions are such that this water is removed as it is formed. Presumably the first principal reaction that occurs, following salt formation, is the formation of a half amide

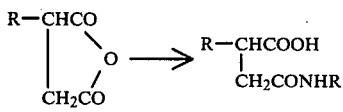

followed then by salt formation

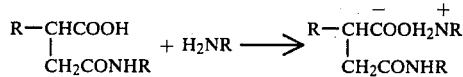

and involving finally dehydration of this salt to form the product

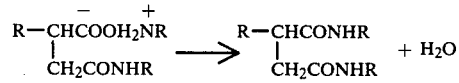

The first two of these reactions appear to take place spontaneously (when a substituted succinic anhydride is used) upon mixing, but the third requires heating. Temperatures within the range of about 80° C. to about 200° C. are satisfactory, and within this range it is preferred to use a reaction temperature of from about 100° C. to about 160° C. A useful method of carrying out this step is to add some toluene to the reaction mixture and to remove the water by azeotropic distillation. As indicated before there is also some imide formation.

It is also believed that in lieu of the ethylene amine reactant, one can use for the purpose of the present invention, any alkylene amine or hydroxyalkyl substituted alkylene amine reactant conforming for the most part to the structure

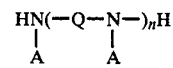

in which n is an integer, A is hydrogen, a hydrocarbon radical, or a hydroxyalkyl radical, and Q is a divalent aliphatic radical containing at least 2 carbon atoms as disclosed in U.S. Pat. No. Re. 26,330. The A substituents in the above formula can also be considered as forming a divalent alkylene radical, in which instance a cyclic structure results. Q is generally an alkylene radical such as ethylene, trimethylene, tetramethylene, etc., although in certain instances it may be an aliphatic radical which contains ether or sulfide substituents such as, e.g., analkylene-O-alkylene-or-alkylene-S-alkylene-radical.

Specific examples of such amine reactants are trimethylene diamine, di-(trimethylene)triamine, tris-(trimethylene) tetramine, tri(hexamethylene)tetramine, decamethylene diamine, N-octyl trimethylene diamine, N,N'-dioctyltrimethylene diamine, N-(2-hydroxyethyl-)ethylene diamine, piperazine, 1-(2-aminopropyl) piperazine, 1,4-bis-(2-aminoethyl)piperazine, 1-(2-hydroxyethyl) piperazine, di(hydroxypropyl) substituted tetraethylene pentamine, N-3-(hydroxypropyl)tetramethylene diamine, pyrimidine, 2-methyl-imidazoline, polymerized ethylene imine, and 1,3-bis-(2-aminoethyl-)imidazoline.

Specific examples of acylated amines which are disclosed in detail in U.S. Pat. No. 3,172,892 and which are useful as the acylated amine herein are shown in Table 1 below.

Thus, another embodiment of the present invention is a method for inhibiting or preventing the accumulation of oxygenated phosphorus compound impurities in the distillation columns and column reboiler units associated with the separation and purification of O,O-dialkyl phosphorochloridothioates from a crude feed stock containing said O,O-dialkyl phosphorochloridothioates admixed with said deposit-forming and fouling-causing oxygenated phosphorus compound impurities which comprises distilling said O,O-dialkyl phosphorochloridothioates containing feed stock in the presence of a minor proportion of an acylated amine prepared by mixing a substituted succinic compound selected from the calss consisting of substituted succinic acids having the structural formula:

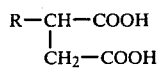

and substituted succinic anhydrides having the structural formula:

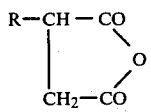

in which structural formulas R is a large, substantially aliphatic hydrocarbon radical having at least about 50 carbon atoms, with at least about one-half an equivalent amount of a hydroxyalkyl-substituted alkylene amine and heating the resulting mixture to effect acylation and remove the water formed thereby.

Such acylated amines have found use in the prior art as hydrocarbon feed stock additives for inhibiting the accumulation of carbonaceous material in refinery cracking units as disclosed, for example, in aforementioned U.S. Pat. No. Re. 26,330 and as dispersing agents in lubricating compositions as disclosed in aforementioned U.S. Pat. No. 3,172,892.

and subsequently fouling the process equipment used in the separation and purification of the desired dialkyl phosphorochloridothioate product from the crude feedstock. Further, the impurities can be readily removed from the column bottoms with the waste stream leaving the columns and column reboilers clean. In terms of the total weight of the feed stock, the amount of additive can range, in general, from about 0.05 to about 15.0 weight percent of additive. Although a definite range has been expressed, it should be noted that the lower limit is that only necessary to react with substantially all of the oxygenated phosphorus compound impurities while the upper limit is defined by practical considerations of the separation technique employed, cost of the additive reagent, equipment size, etc. Further, the amount of treating agent required will vary with the amount of impurities present in individual feedstocks. That is, the amount of additive required depends on the degree of purity of the crude. Crudes containing fewer impurities will require treatment with a smaller amount of additive than crudes containing greater amounts of impurities. A more preferred range of additive treatment level is from about 0.1 to about 10.0 weight percent of additive based on the total weight of the crude.

The treatment of crude dialkyl phosphorochloridothioates with acylated amine is generally effective in reasonably short times at somewhat elevated temperatures. However, the time and temperature relationship can be adjusted to produce effective impurity removal

TABLE I

| Example No. of U.S. Pat. No. 3,172,892 | Acylated Amine Prepared From - | | | |
|---|---|---|---|---|
| | Succinic compound | Equivalents | Amine | Equivalents |
| 1 | Polyisobutene[1] substituted succinic anhydride | 1.0 | Diethylene triamine | 1.0 |
| 2 | Polyisobutene[1] substituted succinic anhydride | 1.0 | Ethylene diamine | 1.0 |
| 3 | Polyisobutene[1] substituted succinic anyhydride | 1.0 | An ethylene amine mixture corresponding to triethylene tetramine | 1.5 |
| 4 | Polyisobutene[1] substituted succinic anhydride | 1.0 | Triethylene tetramine | 1.5 |
| 5 | Polyisobutene[1] substituted succinic anhydride | 0.78 | "Polyamine H" | 1.55 |
| 6 | Polyisobutene[1] substituted succinic anhydride | 1.0 | Ethylene diamine | 1.5 |
| 7 | Polyisobutene[2] substituted succinic anhydride | 1.0 | "Polyamine II" | 1.0 |
| 10 | Polypropylene[3] substituted succinic anhydride | 0.52 | " | 0.52 |
| 12 | Isobutene-styrene copolymer[4] substituted succinic anhydride | 0.51 | "Polyamine II" | 0.51 |
| 17 | polyisobutene[5] substituted succinic anhydride | 2.55 | " | 2.55 |

[1]Polymer contains an average of about 60 carbon atoms.
[2]Polymer contains an average of about 71 carbon atoms.
[3]Polymer contains an average of about 62 carbon atoms.
[4]Copolymer contains an average of about 86 carbon atoms and a weight ratio of isobutene units: styrene units of 94.6.
[5]Polymer contains an average of about 3,600 carbon atoms.

Additives which have been found to be particularly useful in the practice of the present invention can be obtained from Edwin Cooper, Inc., St. Louis, Mo. under the trade names Hitec-664 and Hitec-638.

The additive agents described above are useful in treating the dialkyl phosphorochloridothioate in amounts sufficient for good reaction with the oxygenated phosphorus compound impurities so that such impurities are maintained at a sufficiently fluid state that they are normally dissolved or suspended in the crude feedstock thereby forming a fairly homogeneous phase. As aforediscussed, under these conditions, the impurities will be prevented or hindered from depositing in at low temperatures and relatively longer contact periods or conversely at high temperatures in relatively shorter contact periods. In general, treatment with acylated amine occurs at 100° C. up to temperatures at which the dialkyl phosphorochloridothioate severely thermally degrade. Such higher temperatures should be avoided to prevent the danger of explosive decomposition. Generally, temperatures from 100° C. to about 130° C., depending upon the particular alkyl groups in the product dialkyl phosphorochloridothioate, can be used. The product having the shorter alkyl groups should be kept nearer the lower end of the temperature range, while products having longer chain alkyl groups can withstand temperatures nearer the high end of the temperature range. Contact periods from a few minutes to about one hour or more are typical, depending upon the specific additive composition, the separation system, the temperature, etc. It is only necessary to select these parameters and follow the reaction by sampling over time to establish the point at which substantially all of the impurities have disappeared or dissolved in order to establish a treatment procedure.

The prior art contains adequate teaching for separating product dialkyl phosphorochloridothioate from sulfur, reaction mixture, solvent, etc. Such techniques are useful for separating the reaction product of the additive agent and impurities also. Thus, after treatment with a suitable additive the resultant dialkyl phosphorochloridothioate reaction mixture can be heated to distill off the desired dialkyl phsophorochloridothioate. In a preferred aspect of this process after treatment with additive, the resultant mixture of additive and crude dialkyl phosphorochloridothioate containing oxygenated phosphorus impurities is fed to a distillation section of conventional design, and the dialkyl phosphorochloridothioate is taken overhead as a product substantially free of oxygenated phosphorus compound impurities and the reaction product of such impurities with the additive remains with the bottoms product. The distillation section can be designed and operated in a manner such that substantially low losses of product dialkyl phosphorochloridothioate are incurred and fouling of the process equipment due to the presence of oxygenated phosphorus compounds is virtually eliminated.

As a further illustration describing the process of this invention, the following non-limiting examples are provided. The examples are to be considered only illustrative of the process of this invention. All percentages are by weight unlesss otherwise noted.

COMPARATIVE EXAMPLE 1

This example demonstrates the problem of column reboiler plugging during the separation and purification of product diethyl phosphorochloridothioate from an untreated mixture thereof containing certain phosphorus compound impurities.

Product diethyl phosphorochloridothioate was recovered from untreated crude feedstock by vacuum distillation. A 4" pyrex pipe packed column having about 8 theoretical separation stages and a feed point at about the mid-point of the column above the reboiler was set up to operate at an overhead condenser pressure of approximately 15 mm Hg absolute and an overhead temperature of approximately 84° C. The pressure below the bottom of the packing was 21 mm Hg and the sump temperature was 132° C., produced by approximately 50–70 psig of steam. A feed rate was typically 6.3 pounds per hour of crude diethyl phosphorochloridothioate from which any reaction solvent and lower boiling impurities had already been removed. The column reboiler was an S.S. American Standard exchanger consisting of 3¾ inch diameter tubes; 2 feet 8 inches in length having a heat transfer surface area of 0.8 square feet. A typical feed to the column taken from the column balance follows:

| Component | Weight % |
|---|---|
| DECTP[a] | 59.23 |
| DECP[b] | 0.19 |
| TETP[c] | 0.13 |
| Sulfur Solubizing Agent[d] | 12.95 |
| Other Phosphorus Compounds | 13.77 |
| Sulfur | 4.4 |
| Antifouling Agent[e] | 0.89 |
| Heavy Impurities Treating Agent | 8.44 |
| | 100.00 |

[a]DECTP is diethyl chlorothiophosphate (i.e., diethyl phosphorochloridothioate)
[b]DECP is diethylchlorophosphate
[c]TETP is triethylthiophosphate
[d]Naphthalenic liquid hydrocarbon
[e]Hitec-644

Prior to the addition of acylated amine, the distillation of crude feed streams, similar to the composition given above but without the antifouling agent were run under the given column conditions. Distillation was continued until plugging of the reboiler unit forced the shutdown of the column. After approximately 37 hours of operation the column reboiler was plugged and operation had to be discontinued. As demonstrated by this test, untreated crude plugged the column reboiler in the distillation column and caused eventual involuntary shutdown of the distillation process.

EXAMPLE 2

This example demonstrates that treatment of diethyl phosphorochloridothioate with an acylated amine of the present invention prevents and/or retards column reboiler fouling thereby allowing the long term continuous distillation of diethyl phosphorochloridothioate containing crude without having to interrupt and halt distillation because of column reboiler plugging. In essence, the procedure set forth in Example 1 above was repeated with the exception that approximately 0.4 weight percent of the aforedescribed Hitec-664 was added to the crude feed supplied to the distillation column. The distillation equipment was identical to that described in Example 1 with the exception that the top head on the column reboiler was modified to reduce the tube sheet to open tube area ratio of 8.33:1 to 4:1 in order to cause complete liquid removal with effluent vapor therefrom. After 220 hours of continuous operation, the column was voluntarily shutdown and the reboiler inspected. Two of the 3 tubes in the column reboiler were somewhat fouled but no plugging was observed and the top tube sheet was clean. The bottom head had collected solids but still permitted flow therethrough. From these results, it is clear that the addition of an acylated amine as disclosed in the present invention to a crude feed stock prior to introducing the feed stock into a distillation column for the purpose of separating and purifying product diethyl phosphorochloridothioate from the crude, prevents and/or reduces plugging of the column reboiler associated with the separation and purification of the product diethyl phosphorochloridothioate and thereby accomplishes the objectives of the present invention stated hereandabove.

Having described the invention, one skilled in the art could ascertain various changes and modifications thereof which are within the scope of the disclosed process. Therefore, it is desired to limit the invention only by the lawful scope of the following claims.

I claim:

1. A method for inhibiting or preventing the accumulation of oxygenated phosphorus compound impurities in the distillation columns and column reboiler units associated with the separation and purification of O,O-dialkyl phosphorochloridothioates from a crude feed stock containing said O,O-dialkyl phosphorochloridothioates admixed with said deposit-forming and fouling-causing oxygenated phosphorus compound impurities which comprises distilling said O,O-dialkyl phosphorochloridothioate containing feed stock in the presence of a minor proportion of an acylated amine prepared by mixing a substituted succinic compound selected from the class consisting of substituted succinic acids having the structural formula:

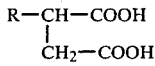

and substituted succinic anhydrides having the structural formula:

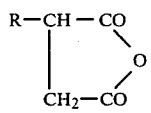

in which structural formulas R is a large, substantially aliphatic hydrocarbon radical having at least about 50 carbon atoms, with at least about one-half an equivalent amount of an ethylene amine and heating the resulting mixture to effect acylation and remove the water formed thereby.

2. The method of claim 1 wherein said O,O-dialkyl phosphorochloridothioate is O,O-di($C_1$–$C_8$ alkyl) phosphorochloridothioate.

3. The method of claim 1 wherein said O,O-dialkyl phosphorochloridothioate is diethyl phosphorochloridothioate.

4. The method of claim 1 wherein said O,O-dialkyl phosphorochloridothioate is dimethyl phosphorochloridothioate.

5. The method of claim 1 wherein said oxygenated phosphorus compound impurity is a diethyl or dimethyl phosphate impurity.

6. The method of claim 1 wherein said oxygenated phosphorus compound impurity is diethyl phosphate impurity.

7. The method of claim 1 wherein said oxygenated phosphorus compound impurity is diethyl chlorophosphate.

8. The method of claim 1 in which said distillation is carried out in the presence of at least about 0.05 weight percent of said acylated amine based on the total weight of said feedstock.

9. The method of claim 1 in which said distillation carried out in the presence of at least from about 0.05 weight percent to about 15.0 weight percent of said acylated amine based on the total weight of said feedstock.

10. The method of claim 1 wherein the large substantially aliphatic hydrocarbon radical is derived from a polyisobutene.

11. The method of claim 1 wherein the ethylene amine is diethylene triamine.

12. The method of claim 1 wherein the ethylene amine is triethylene tetramine.

13. The method of claim 1 wherein the ethylene amine is a mixture of diethylene triamine and triethylne tetramine.

14. The method of claim 1 wherein the ethylene amine is a mixture of ethylene amines having a composition corresponding to tetraethylene pentamine.

15. The method of claim 1 wherein the acylated amine is prepared by mixing a substituted succinic anhydride having the structural formula:

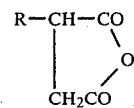

wherein R is a large, substantially aliphatic hydrocarbon radical having at least about 50 carbon atoms, said substituted succinic anhydride having been prepared by the reaction of maleic anhydride with a high molecular weight olefin; with at least about one-half an equivalent amount per equivalence of substituted succinic anhydride, of an ethylene polyamine, and heating the resulting mixture within the temperature range of from about 80° C. to about 200° C. to effect acylation and to remove the water formed thereby.

16. The method of claim 1 wherein the acylated amine is prepared by mixing a substituted anhydride having the structural formula:

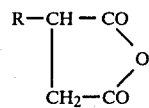

wherein R is a large, substantially aliphatic hydrocarbon radical having at least about 50 carbon atoms, said substituted succinic anhydride having been prepared by the reaction of maleic anhydride with a chlorinated high molecular weight olefin; with at least about one-half an equivalent amount, per equivalent of substituted succinic anhydride, of an ethylene polyamine, and heating the resulting mixture within the temperature range of from about 80° C. to about 200° C. to effect acylation and to remove the water formed thereby.

17. The method of claim 16 wherein R is a polyisobutenyl radical having at least about 50 carbon atoms.

18. A method for inhibiting or preventing the accumulation of oxygenated phosphorus compound impurities in the distillation columns and column reboiler units associated with the separation and purification of O,O-dialkyl phosphorochloridothioates from a crude feed stock containing said O,O-dialkyl phosphorochloridothioates admixed with said deposit-forming and fouling-causing oxygenated phosphorous compound impurities which comprises distilling said O,O-dialkyl phosphorochloridothioate containing feed stock in the presence of a minor proportion of an acylated amine prepared by mixing a substituted succinic compound selected from the class consisting of substituted succinic acids having the structural formula:

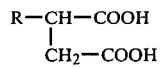

and substituted succinic anhydrides having the structural formula:

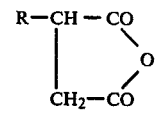

in which structural formulas R is a large, substantially aliphatic hydrocarbon radical having at least about 50 carbon atoms, with at least about one-half an equivalent amount of a hydroxyalkyl substituted alkylene amine and heating the resulting mixture to effect acylation and remove the water formed thereby.

* * * * *

UNITED STATES PATENT AND TRADEMARK OFFICE
CERTIFICATE OF CORRECTION

PATENT NO. : 4,292,139
DATED : September 29, 1981
INVENTOR(S) : Ellis B. Rifkin

It is certified that error appears in the above—identified patent and that said Letters Patent are hereby corrected as shown below:

Column 3, line 62 - "where" should be -- there --
Column 11, line 1 - "calss" should be -- class --
Column 11, line 59 - "Hitec 664" should be -- Hitec 644 --
Column 14, line 39 - "Hitec 664" should be -- Hitec 644 --

Signed and Sealed this

Twenty-second Day of December 1981

|SEAL|

Attest:

GERALD J. MOSSINGHOFF

Attesting Officer     Commissioner of Patents and Trademarks